(12) United States Patent
Wagenleitner et al.

(10) Patent No.: US 11,970,366 B2
(45) Date of Patent: Apr. 30, 2024

(54) HANDRAIL DISINFECTING DEVICE FOR PASSENGER TRANSPORT INSTALLATIONS

(71) Applicant: INVENTIO AG, Hergiswil (CH)

(72) Inventors: Georg Wagenleitner, Roßleithen (AT); Gerhard Kleewein, Pressbaum (AT); Michael Berger, Königstetten (AT); Richard Schütz, Vienna (AT); Ulrich Häberle, Purkersdorf (AT)

(73) Assignee: Inventio AG, Hergiswil (CH)

( * ) Notice: Subject to any disclaimer, the term of this patent is extended or adjusted under 35 U.S.C. 154(b) by 60 days.

(21) Appl. No.: 17/802,801

(22) PCT Filed: Mar. 9, 2021

(86) PCT No.: PCT/EP2021/055915
§ 371 (c)(1),
(2) Date: Aug. 26, 2022

(87) PCT Pub. No.: WO2021/190915
PCT Pub. Date: Sep. 30, 2021

(65) Prior Publication Data
US 2023/0143319 A1    May 11, 2023

(30) Foreign Application Priority Data

Mar. 25, 2020   (EP) .................................... 20165562

(51) Int. Cl.
*B66B 31/02*   (2006.01)
*A61L 2/10*   (2006.01)
(Continued)

(52) U.S. Cl.
CPC ............... *B66B 31/02* (2013.01); *A61L 2/10* (2013.01); *A61L 2/26* (2013.01); *B65G 45/10* (2013.01);
(Continued)

(58) Field of Classification Search
CPC . B65G 45/10; B66B 31/02; A61L 2/10; A61L 2/26; A61L 2202/11; A61L 2202/122
(Continued)

(56) References Cited

U.S. PATENT DOCUMENTS 11,174,131 B1 * 11/2021 Gonzalez .................. A61L 2/10
11,479,168 B2 * 10/2022 Vorac ...................... B60Q 3/68
(Continued)

FOREIGN PATENT DOCUMENTS

CN          111332930 A  *  6/2020  ............. B66B 31/02
DE   102010018227 A1  *  10/2011  ............. B66B 31/02
(Continued)

OTHER PUBLICATIONS

International Search Report for International Application No. PCT/EP2021/055915 dated Jun. 4, 2021.

*Primary Examiner* — James R Bidwell
(74) *Attorney, Agent, or Firm* — Knobbe, Martens, Olson & Bear, LLP (57) ABSTRACT

The disclosure relates to a handrail disinfecting device for a handrail of a passenger transport installation. The handrail disinfecting device has a plurality of light-emitting diodes that can emit germicidal electromagnetic radiation in the region of their light cone. A pass-through segment of the handrail disinfecting device is divided into at least two sectors and has a carrier having planes that are arranged in the sectors. The light-emitting diodes are arranged on the carrier such that they are oriented according to the planes. In one of the sectors, there are two planes that are arranged in parallel with the longitudinal extension of the pass-through segment and so as to be mutually inclined at an angle of 100° to 160°.

15 Claims, 5 Drawing Sheets

(51) Int. Cl.
*A61L 2/26* (2006.01)
*B65G 45/10* (2006.01)
*B66B 23/24* (2006.01)

(52) U.S. Cl.
CPC .......... *B66B 23/24* (2013.01); *A61L 2202/11* (2013.01); *A61L 2202/122* (2013.01)

(58) Field of Classification Search
USPC ................................................ 198/494, 337
See application file for complete search history.

(56) References Cited

U.S. PATENT DOCUMENTS

| | | | |
|---|---|---|---|
| 11,565,012 B2 * | 1/2023 | Grenon | G01J 1/429 |
| 11,707,545 B2 * | 7/2023 | Kim | A61L 2/04 |
| | | | 250/455.11 |
| 2006/0175177 A1 * | 8/2006 | Lombard | B66B 31/02 |
| | | | 198/494 |
| 2012/0211645 A1 * | 8/2012 | Tullo | B65G 45/10 |
| | | | 250/492.1 |
| 2015/0028228 A1 | 1/2015 | Almasy et al. | |

FOREIGN PATENT DOCUMENTS

| | | | | |
|---|---|---|---|---|
| JP | H 08188369 A | 7/1996 | | |
| JP | 2016124660 A | 7/2016 | | |
| KR | 101415154 B1 | 7/2014 | | |
| KR | 20150114933 A | 10/2015 | | |
| WO | 2011131744 A1 * | 10/2011 | ............. | B66B 31/02 |
| WO | WO 2019112356 A1 | 6/2019 | | |
| WO | WO 2019/164256 A1 | 8/2019 | | |

\* cited by examiner

HANDRAIL DISINFECTING DEVICE FOR PASSENGER TRANSPORT INSTALLATIONS

TECHNICAL FIELD

The present disclosure relates to a handrail disinfecting device, comprising at least one housing and a plurality of light-emitting diodes that can emit germicidal electromagnetic radiation, to a passenger transport installation having at least one handrail disinfecting device, and to a method for controlling the handrail disinfecting device.

SUMMARY

Passenger transport installations that are designed as escalators or moving walkways usually have circulating handrails that move at the same speed as the conveyor belt on which the user can stand. This allows users to hold onto the handrails while moving. The region of the handrail where the user can hold on is referred to as the leading run, while the returning run is concealed from the users of the passenger transport installation and is returned against the direction of transport. When users' hands touch the surface of the handrails, bacteria, germs, and viruses get onto the handrail. The pathogens deposited in this way can multiply on the handrail and be transmitted to subsequent users. The handrail of such a passenger transport installation thus represents an unhygienic place in public space where infectious diseases can be transmitted.

WO2019/164256A1 discloses a handrail disinfecting device according to the prior art. Here, a handrail is irradiated with ultraviolet light using light-emitting diodes. This germicidal electromagnetic radiation destroys the deoxyribonucleic acid of viruses and bacteria so that a significant reduction in microorganisms can be detected on the surface of the handrail from the exit side of this handrail disinfecting device.

JP08188369A, for example, provides for extensive pre-cleaning with rotating brushes and a washing system with germicidal fluids, such that the cleaned surface of the handrail can then be disinfected by the radiation from the UV lamp in order to allow for even more thorough disinfection. However, such a handrail disinfecting device is very expensive and, in particular because of the fluids required, results in high operating costs.

The object of the present disclosure is therefore to render the pathogens on the handrails harmless even more reliably by means of a cost-effective and simple handrail disinfecting device.

This object is achieved by a handrail disinfecting device that comprises at least one housing and a plurality of light-emitting diodes, wherein the light-emitting diodes each having a main light cone axis that represents the orientation of the light cone of the light-emitting diode. The light-emitting diodes can emit germicidal electromagnetic radiation in the region of their light cone. The housing has an entry side and an exit side opposite the entry side for a continuous handrail of a passenger transport installation. A pass-through segment for the handrail, which segment is divided into at least two sectors, is present in the housing of the handrail disinfecting device between the entry side and the exit side. These sectors are arranged one behind the other in the longitudinal extension of the pass-through segment. At least one light-emitting diode is arranged in the first sector, the main light cone axis of which diode is oriented substantially orthogonally to a first plane. Furthermore, at least two light-emitting diodes are arranged in the second sector, wherein the main light cone axis of at least one light-emitting diode is oriented substantially orthogonally to a second plane and the main light cone axis of at least one light-emitting diode is oriented substantially orthogonally to a third plane. In addition, the second plane and the third plane are arranged in parallel with the longitudinal extension of the pass-through segment and so as to be mutually inclined at an angle of 100° to 160°. The first plane is preferably arranged relative to the handrail in such a way that the surface mainly touched by the users is irradiated as directly as possible by the light-emitting diodes of said plane. To ensure that the distance between the surfaces to be disinfected and the light-emitting diodes is as constant as possible and thus to achieve a constant disinfection quality, the handrail disinfecting device has at least one guide roller, by means of which guide roller the handrail of the passenger transport installation can be guided through the housing in the pass-through segment in a defined position.

Studies have shown that despite the deadly electromagnetic radiation, the microorganisms have a certain chance of survival. This depends in particular on the surface finish and the cleanliness of the handrail to be disinfected. Zones in which the microorganisms can survive can be shaded by cracks, gaps, notches, pits and the like, as well as by adhering dirt particles. Although, as disclosed in JP08188369A, these zones can also be reached by mechanical pre-cleaning with rotating brushes and by washing the handrail surface, the quality of the cleaning and disinfection depends to a large extent on the regular and reliable maintenance of such a handrail disinfecting device.

The present disclosure takes a different approach by dividing the pass-through segment into sectors in a suitable manner and using planes fitted with light-emitting diodes arranged at different angles in said sectors to achieve almost complete and, over the duration of the exposure, sufficient irradiation of a handrail surface that is covered with dirt particles and has cracks and pits. As a result, maintenance-intensive and expensive pre-cleaning can be dispensed with. An obtuse-angled arrangement of at least two planes at 100° to 160° to one another has proven to be particularly suitable. Ultraviolet light having a wavelength of 220 nm to 285 nm, for example, has proven to be very efficient as germicidal electromagnetic radiation. This is supported by the advantageous guidance of the handrail by means of at least one guide roller, as a result of which the surface of the handrail passing the light-emitting diodes is always guided in the same position in the pass-through segment in relation to the light-emitting diodes.

In one embodiment of the handrail disinfecting device, at least one guide roller is arranged on the entry side and/or on the exit side. The appropriate number of guide rollers depends substantially on the length of the pass-through segment and the stiffness of the handrail.

In a further embodiment of the handrail disinfecting device, the at least one guide roller can also be arranged inside the housing and thus in the pass-through segment. Of course, combinations of these arrangements are also possible, such that, for example, one guide roller each is arranged on the entry side and on the exit side and one or more guide rollers are arranged in the housing between said sides.

The division into sectors has other advantages. The surface of the handrail heats up as a result of the radiation, depending on the wavelength of the electromagnetic radiation, the angle of incidence on the surface and the material properties of the handrail. Some heating-up is desirable, as many viruses are sensitive to heat and most are inactivated at temperatures above 70° Celsius. Owing to the pass-through segment divided into sectors, the surface of the handrail can be heated sequentially such that, in addition to the germicidal radiation effect, a higher temperature can be maintained over a longer period of time without the handrail material being heated too much and thus aging more quickly.

Depending on the control of the individual sectors, a desired temperature profile can be achieved over the entire pass-through segment. Particles such as metal particles, silver ions and the like that are tuned to the electromagnetic waves can optionally be more embedded in the material of the handrail, in particular in its surface, which particles heat up additionally due to the radiation and emit heat over a longer period of time.

In a further embodiment of the handrail disinfecting device, the inclination of the second plane relative to the first plane is the same as the inclination of the third plane relative to the first plane. In this way, symmetrical irradiation that is the same across the width of the handrail can be achieved. In the case of asymmetrical handrail cross sections, an asymmetrical arrangement of the second and the third plane with respect to the first plane may also be suitable.

In a further embodiment of the handrail disinfecting device, a third sector can be defined in the pass-through segment, in which sector at least one light-emitting diode is arranged, the main light cone axis of which is oriented orthogonally to a fourth plane. In this case, the second sector is arranged between the first and the third sector, and the fourth plane is arranged in parallel with the first plane. As a result, the surface that is touched particularly intensively by users can be irradiated again before it leaves the handrail disinfecting device.

In a further embodiment of the handrail disinfecting device, at least three light-emitting diodes can be arranged in each plane, wherein the main light cone axes are oriented substantially in parallel with one another in each plane. In this case, "substantially in parallel" means that the main light cone axes in a plane can spatially deviate from parallelism by up to 3°. This may well be intentional with regard to even more efficient irradiation in the case of overlapping light cones. Very good results with low energy consumption have been achieved, for example, with a handrail disinfecting device of the aforementioned type that has five light-emitting diodes in the first plane and three light-emitting diodes each in the second and the third plane. By the arrangement of a fourth plane in which four light-emitting diodes are arranged, it was possible to achieve excellent disinfection performance with only slightly increased energy consumption.

In a further embodiment of the handrail disinfecting device, the housing is designed in two parts, wherein said housing has a U-shaped main housing part and a cover spanning the open side of the main housing part. This division makes it easy to insert a handrail into the housing if the handrail has to be replaced due to age. In addition, the pass-through segment of the housing can be cleaned more easily and defective light-emitting diodes can be replaced more easily.

In a further embodiment, the handrail disinfecting device comprises a carrier that is arranged in the housing below the pass-through segment with respect to the intended installation position of the handrail disinfecting device. All existing planes can be formed on this carrier, wherein the light-emitting diodes are fastened to said planes. As a result, the arrangement of the planes relative to one another is fixed. The light-emitting diodes are optionally fastened to one or more printed circuit boards, which are arranged on the planes. In order to dissipate the heat from the light-emitting diodes, the printed circuit board and/or the carrier can have heat sinks.

In a further embodiment of the handrail disinfecting device, at least one reflector which is directed toward the pass-through segment and is intended for reflecting the radiation is arranged in the housing. As a result, electromagnetic radiation that has been reflected by the handrail surface or that hits the inside of the housing past the handrail can be directed onto the handrail in order to further increase the disinfection performance. In order to simplify the cleaning of the reflector, it can preferably be fastened to the above-described cover of the housing.

As already mentioned, the division into a plurality of sectors and in these differently arranged planes is intended to achieve the most comprehensive possible irradiation of the surface of the handrail. Accordingly, it is also advantageous if the surface of the handrail always moves through the pass-through segment at equal distances from the planes.

Handrails for passenger transport installations usually have a C-shaped cross section, with the most touched and therefore most contaminated region being the broad rear surface. Said broad rear surface is preferably supported by the guide roller and is irradiated as directly as possible by the light-emitting diodes arranged on the first plane by the main light cone axes of said diodes being directed as orthogonally as possible to this region. In order to achieve this, an axis of rotation of the guide roller is preferably arranged in parallel with the first plane and orthogonally to the pass-through segment.

Furthermore, a tread contour of the guide roller can correspond to an outer surface contour of the handrail to be guided. As a result, the handrail is not only guided with more precise positioning through the housing, but the guide roller having a correspondingly adapted contour also serves as radiation protection because hardly any electromagnetic radiation can escape from the housing through the narrow gap between the handrail and the tread contour.

In a further embodiment of the handrail disinfecting device, the angle of the mutually inclined second and third plane can be matched to the spectral composition of the germicidal electromagnetic radiation and the material composition of the handrail surface. In particular, the heating of the surface of the handrail by the electromagnetic radiation, which depends on these factors, must also be taken into account. The appropriate angles can be calculated in a known manner, taking into account the desired irradiation, or they can be determined experimentally.

The embodiment variants of the handrail disinfecting device described above can be used in passenger transport installations that are designed as escalators or moving walkways. These have at least one balustrade, which comprises at least one circumferential handrail. A passenger transport installation of the aforementioned type usually has two balustrades, each having a circumferentially arranged handrail and being arranged on both sides of a conveyor belt of the passenger transport installation. According to the disclosure, at least one handrail disinfecting device according to one of the embodiments described above is provided for each circulating handrail of a passenger transport installation.

The passenger transport installation can comprise a balustrade having a balustrade base in which a returning run of the handrail is concealed from the users of the passenger transport installation. In order to best protect users from the germicidal electromagnetic radiation, the handrail disinfecting device can be installed in the balustrade base of the balustrade. As a result, not only does the housing shield the environment from this radiation, which is harmful to organisms of all kinds, but the casing of the balustrade base also acts as a second barrier.

The division into sectors also offers the possibility of operating the handrail disinfecting device in different operating modes adapted to the place of use and the use profile of the passenger transport installation. For this purpose, a method for controlling the handrail disinfecting device can be implemented in a controller of the passenger transport installation. The passenger transport installation has a drive motor for driving the handrail and a drive controller for controlling the drive motor. Because the disinfecting effect of the handrail disinfecting device also depends on the throughput speed of the handrail, the light-emitting diodes of the individual sectors can be controlled sector by sector according to a speed signal from the drive controller to the drive motor.

BRIEF DESCRIPTION OF THE DRAWINGS

Embodiments of the disclosure will be described below with reference to the accompanying drawings, with neither the drawings nor the description being intended to be interpreted as limiting the disclosure. Furthermore, the same reference signs are used for elements that are identical or have the same effect. In the drawings.

DETAILED DESCRIPTION

Figure 1:
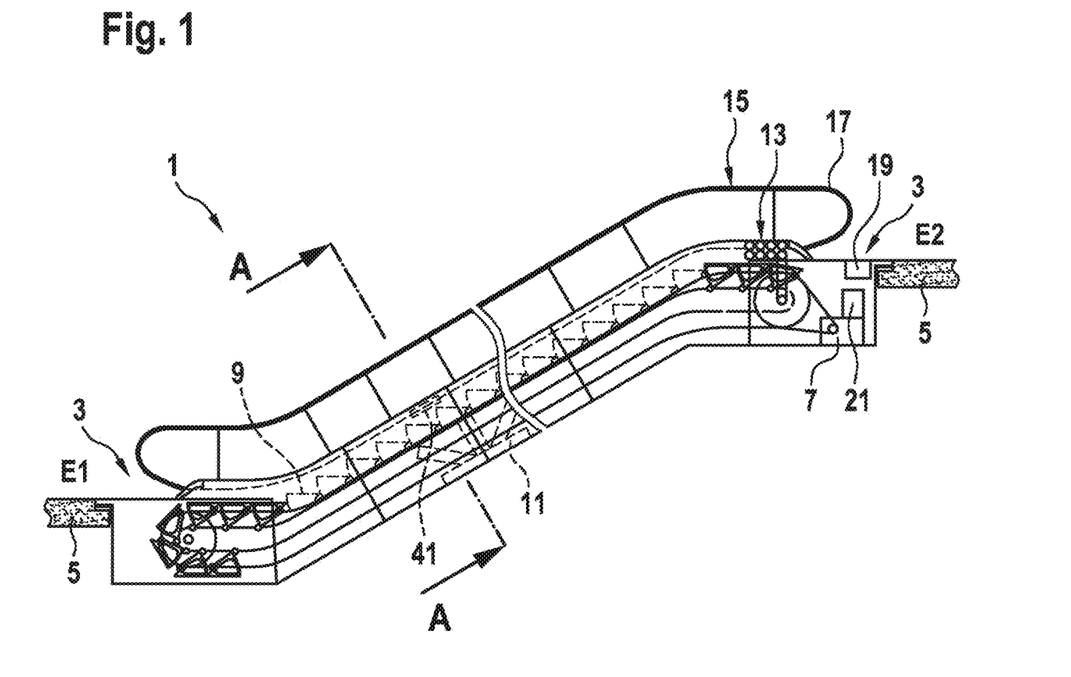
FIG. 1 is a simplified view of a passenger transport installation designed as an escalator and having a handrail disinfecting device.

FIG. 1 shows a simplified view of a passenger transport installation 1 having a supporting structure 11 designed as a framework. The passenger transport installation 1 designed as an escalator connects a lower level E1 with an upper level E2 of a building 5. The passenger transport installation 1 can be entered and exited again via access regions 3. A circulating step belt 9 is arranged in the supporting structure 11, which step belt is deflected in the upper level E2 and in the lower level E1 and thus has a leading portion and a returning portion. For the sake of a better overview, the detailed representation of the returning portion, as well as a detailed representation of frames, guide rails, and rail blocks, has been omitted. The passenger transport installation 1 also has two balustrades 15 that extend along each longitudinal side of the step belt 9, with only the balustrade 15 arranged in the foreground in the viewing plane being visible in FIG. 1. A handrail 17 is arranged in a circulating manner on each balustrade 15, the returning run of which handrail is guided in a balustrade base 13. This balustrade base 13 connects the balustrade 15 to the supporting structure 11. In other words, the returning run of the handrail 17 is concealed from the users of the passenger transport installation 1 and is guided in the balustrade base 13.

Furthermore, the passenger transport installation 1 has at least one handrail disinfecting device 41 for each circulating handrail 17. Said device is also installed in the balustrade base 13 of the balustrade 15 and thus concealed from the users of the passenger transport installation 1.

Figure 2:
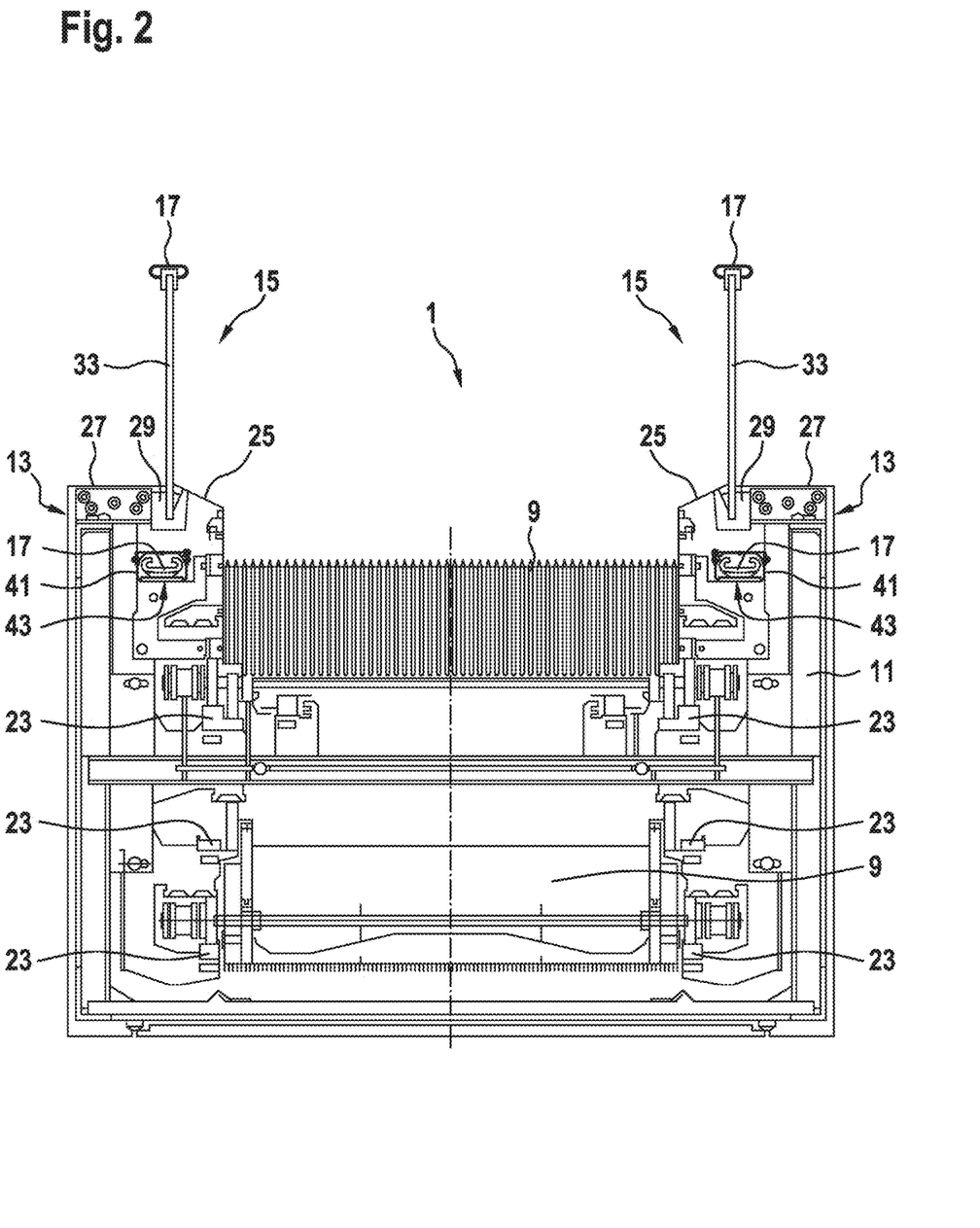
FIG. 2 is a cross section along the line A-A through the passenger transport installation of FIG. 1.

FIG. 2 shows a cross section through the passenger transport installation 1 according to FIG. 1 along the line A-A. In this cross section, both the leading and the returning portion of the step belt 9 can be seen. The step belt 9 is guided on guide rails 23 within the supporting structure 11. A balustrade 15 and a balustrade base 13 are arranged to the left and right of the leading portion of the step belt 9, which portion is arranged at the top when the passenger transport installation 1 is installed as intended. Clamping devices 29 are provided within the balustrade base 13, concealed by cladding panels 25, 27, which serve as clamping receptacles for the individual balustrade panels 33. In this case, the balustrade panel 33 is clamped in a stationary manner at its lower end in at least one of the clamping devices 29. The clamping devices 29 are arranged along the longitudinal extension of the passenger transport installation 1 within the balustrade base 13 on the supporting structure 11. Below the clamping devices 29, a handrail disinfecting device 41 is provided for each handrail 17 arranged in a circulating manner on the balustrade 15, which handrail disinfecting device is equipped with light-emitting diodes 43 that can emit germicidal electromagnetic radiation in the region of their light cone.

Because the returning run of the handrail 17 is also guided in the balustrade base 13, it is advantageous to arrange the handrail disinfecting device 41 in the balustrade base 13 and to guide the returning run through said handrail disinfecting device there. It can thereby be ensured that no harmful electromagnetic radiation can reach the users of the passenger transport installation 1 under any circumstances.

Figure 3:
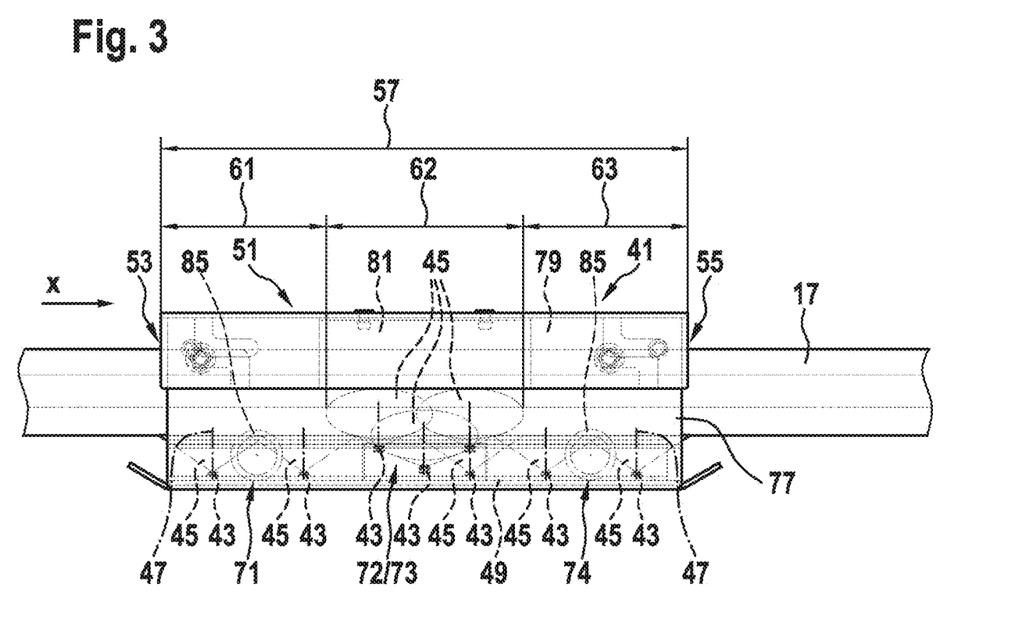
FIG. 3 is a side view of the handrail disinfecting device shown in FIGS. 1 and 2.
Figure 4:
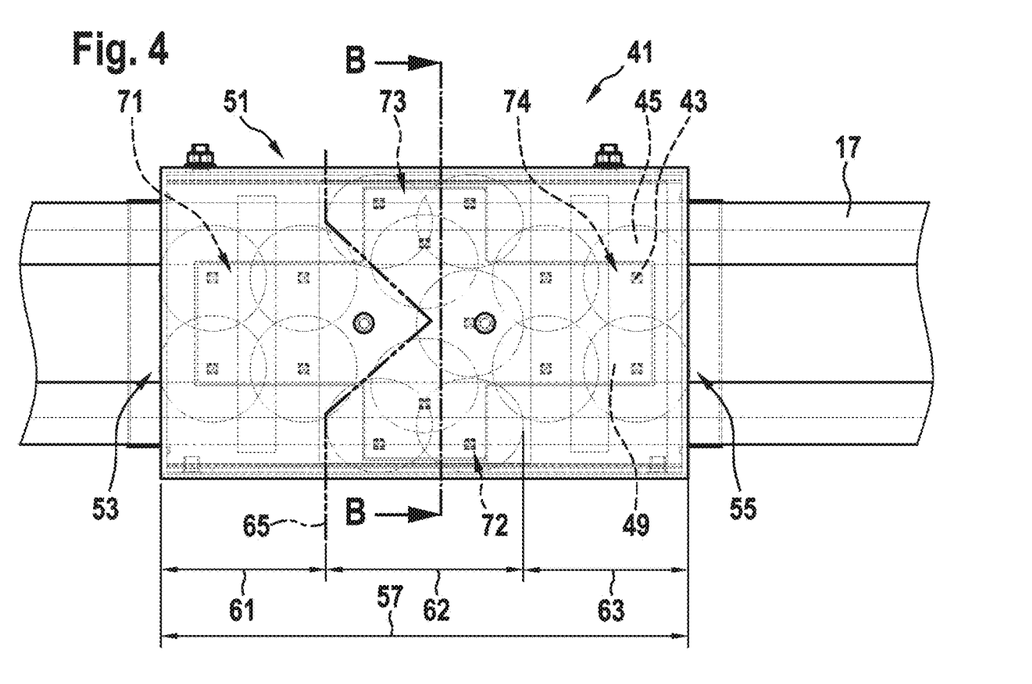
FIG. 4 is a plan view of the handrail disinfecting device of FIGS. 1 to 3.
Figure 5:
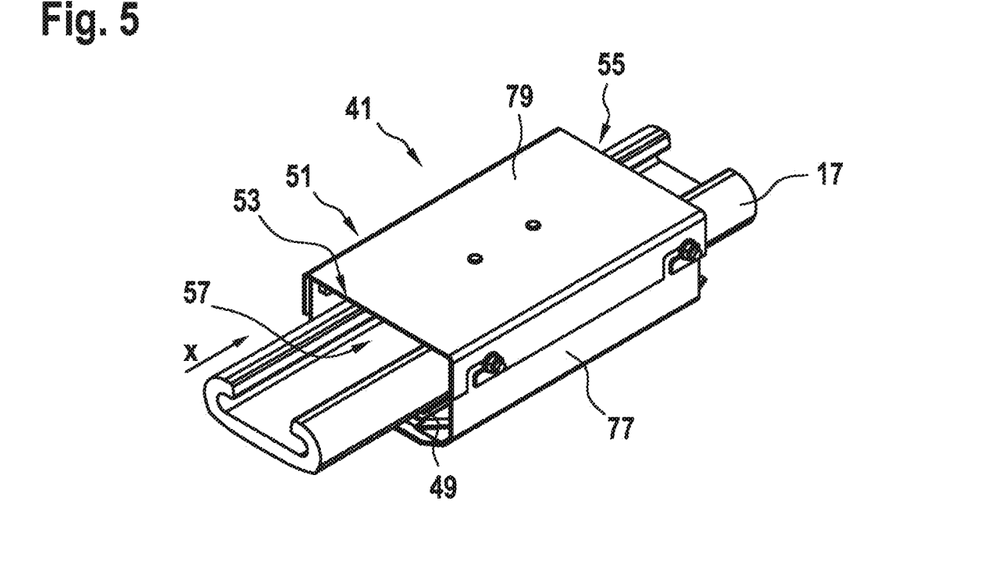
FIG. 5 is a three-dimensional view of the handrail disinfecting device shown in FIGS. 1 to 4 with a guided-through portion of a handrail of the passenger transport installation.
Figure 6:
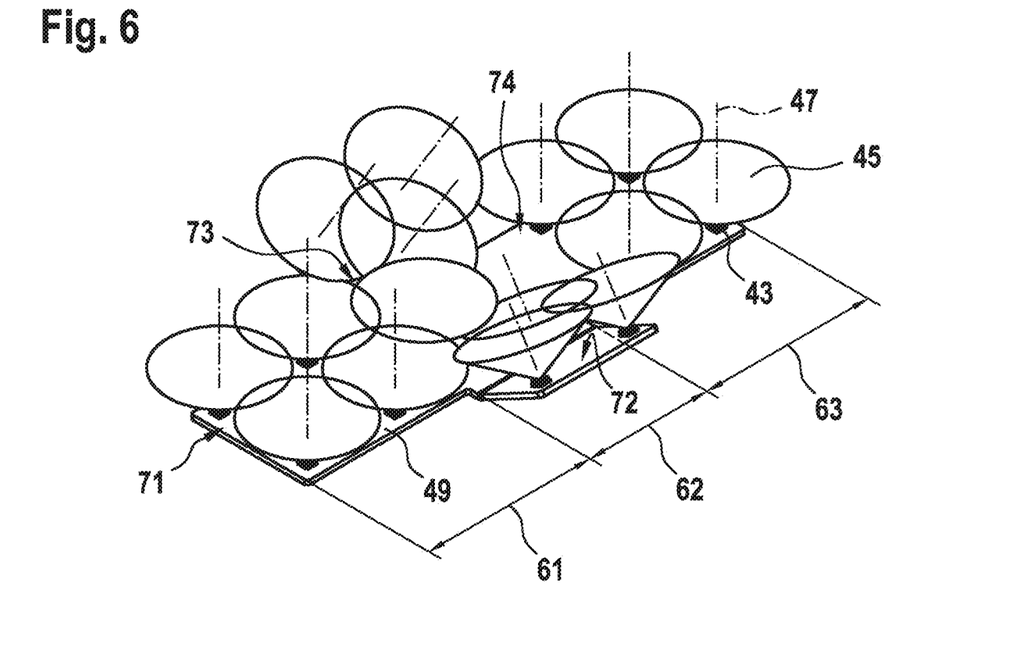
FIG. 6 is a three-dimensional view of a carrier arranged in the handrail disinfecting device of FIGS. 1 to 5 and equipped with light-emitting diodes.
Figure 7:
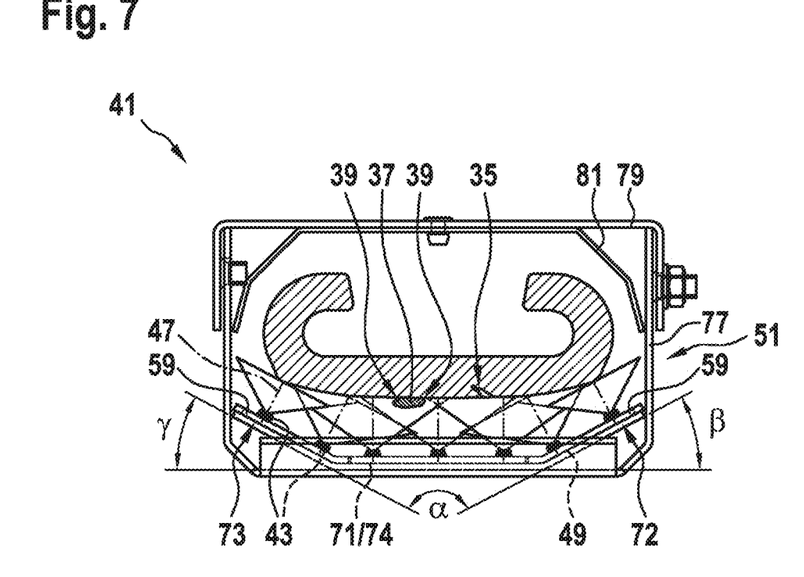
FIG. 7 is a cross section of the handrail disinfecting device shown in FIGS. 1 to 6 along the line B-B shown in FIG. 4.

FIGS. 3 to 7 all show the same handrail disinfecting device 41 already shown in FIGS. 1 and 2, or at least parts thereof. Therefore, these figures are described together below. More precisely, FIG. 3 shows the handrail disinfecting device 41 in a side view, FIG. 4 in a plan view, FIG. 5 in a three-dimensional view; FIG. 6 is a three-dimensional view of a carrier 49 arranged in the handrail disinfecting device 41 and FIG. 7 is a cross section through the handrail disinfecting device 41 along the line B-B shown in FIG. 4.

The handrail disinfecting device 41 shown in these figures, FIGS. 3 to 7, comprises a housing 51 and a plurality of light-emitting diodes 43. Due to their design, the light-emitting diodes 43 have a light cone 45, wherein said light-emitting diodes can emit germicidal electromagnetic radiation in the region of their light cone 45. The spatial orientation of the light cone 45 is represented by a main light cone axis 47, which is also the axis of rotational symmetry of the light cone 45. It should also be noted that the light cones 45 shown have a circular contour that could be regarded as the end face. However, it is clear that this contour is not an end face, but rather a light cone cross section at any cone height in order to be able to visualize the light cone better and should therefore not constitute a limitation of the propagation of electromagnetic radiation.

The housing 51 has an entry side 53 and an exit side 55 opposite the entry side 53 for a continuous handrail 17 of a passenger transport installation 1. Logically, the designations for the entry side 53 and the exit side 55 depend on the direction of movement X of the handrail 17 and change according to said direction of movement. In the housing 51, there is a pass-through segment 57 for the handrail 17 between the entry side 53 and the exit side 55. This pass-through segment 57 is divided into at least two sectors. In the specific embodiment of FIGS. 3 to 7, the pass-through segment 57 is divided into three sectors 61, 62, 63. The sectors 61, 62, 63 are arranged one behind the other in the longitudinal extension of the pass-through segment 57 and are designed to be distinguishable from one another. It should also be noted that the boundaries of the sectors 61, 62, 63 do not necessarily have to be based on orthogonal sectional planes such as the sectional plane B-B shown in FIG. 4. The sector boundary 65 with the double dot-dash line in FIG. 4 between the first sector 61 and the second sector 62 is mentioned as an example, which boundary is adapted to the light-emitting diodes 43 arranged therein.

At least one light-emitting diode 43 is arranged in the first sector 61 in such a way that its main light cone axis 47 is oriented substantially orthogonally to a first plane 71. In the specific embodiment, a total of five light-emitting diodes 43 are arranged in the first sector 61, the main light cone axes 47 of which diodes are arranged substantially orthogonally to the first plane 71 and therefore substantially in parallel with one another.

At least two light-emitting diodes 43 are arranged in the second sector 62 in such a way that the main light cone axis 47 of at least one of said light-emitting diodes 43 is oriented substantially orthogonally to a second plane 72 and the main light cone axis 47 of at least one of said light-emitting diodes 43 is oriented substantially orthogonally to a third plane 73. In the specific embodiment, a total of six light-emitting diodes 43 are arranged in the second sector 62, wherein the main light cone axes 47 of three of said light-emitting diodes 43 are arranged substantially orthogonally to the second plane 71 or substantially in parallel with one another, and the main light cone axes 47 of the other three of said light-emitting diodes 43 are arranged substantially orthogonally to the third plane 73 or substantially in parallel with one another. Furthermore, the second plane 72 and the third plane 73 are arranged in parallel with the longitudinal extension of the pass-through segment 57 and so as to be mutually inclined at an angle α (see FIG. 7). With an obtuse angle α of 100° to 160°, particularly good results could be achieved by the disinfecting effect of the handrail disinfecting device 41. In particular, the angle α of the mutually inclined second and third plane 72, 73 can be matched to the spectral composition of the germicidal electromagnetic radiation and the material surface of the handrail 17.

Furthermore, two guide rollers 85 are arranged in the housing 51 such that a handrail 17 guided through is supported by the guide rollers 85. As a result, the surface of the handrail 17 is irradiated as directly as possible by the light-emitting diodes 43 arranged on the planes 71, 72, 73 by directing the main light cone axes of said diodes as orthogonally as possible relative to the surface of the handrail 17. In order to achieve this, an axis of rotation of the guide roller 85 is preferably arranged in parallel with the first plane 71 and orthogonally to the pass-through segment 57.

FIG. 7 also shows how the irradiation of problem regions such as undercut cracks 35 and edges 39 of dirt particles 37 can be improved by the light-emitting diodes 43 arranged in the second plane 72 and third plane 73.

At least one light-emitting diode 43 is arranged in the third sector 63 of the pass-through segment 57, the main light cone axis 47 of which diode is oriented substantially orthogonally to a fourth plane 74. In the specific embodiment, a total of four light-emitting diodes 43 are arranged in the third sector 63, the main light cone axes 47 of which diodes are arranged substantially orthogonally to the fourth plane 74 or substantially in parallel with one another. In this case, the second sector 62 is arranged between the first sector 61 and the third sector 63, and the fourth plane 74 is arranged in parallel with the first plane 71.

The arrangement of the main light cone axes 47 is therefore "substantially" orthogonal or parallel because slight deviations of up to 3° from parallelism are possible due to production or for intentional reasons. As can be seen in particular from FIG. 7, the inclination β of the second plane 72 to the first plane 71 can be the same as the inclination γ of the third plane 73 to the first plane 71.

The housing 51 of the handrail disinfecting device 41 is designed in two parts. Said housing has a U-shaped main housing part 77 and a cover 79 spanning the open side of the main housing part 77. As a result, the light-emitting diodes 43 arranged in the housing 51 can be replaced more easily and the pass-through segment 57 can be cleaned better.

Furthermore, when a handrail 17 is replaced, it can more easily be removed from the handrail disinfecting device 41 or inserted into the pass-through segment 57 thereof without any risk of damage to the light-emitting diodes 43.

As already mentioned above, the handrail disinfecting device 41 can comprise a carrier 49 (see in particular FIG. 6) that is arranged in the housing 51 below the pass-through segment 57 with respect to the intended installation position of the handrail disinfecting device 41 in a passenger transport installation 1. In the present embodiment, the carrier 49 is fastened in the main housing part 77. All planes 71, 72, 73, 74 present are preferably formed on this carrier 49. The light-emitting diodes 43 are fastened to said planes. In this context, it is irrelevant whether the light-emitting diodes 43 are fastened directly to the carrier 49 or whether, for example, there is a circuit board 59 fitted with the light-emitting diodes 43 for each plane 71, 72, 73, 74, which circuit board is fastened to the relevant plane 71, 72, 73, 74 assigned thereto.

Furthermore, at least one reflector 81 (clearly visible in FIGS. 3 and 7) which is directed toward the pass-through segment 57 and is intended for reflecting the radiation emitted by the light-emitting diodes 43 can be arranged in the housing 51. In the present embodiment, the reflector 81 is fastened in the cover 79.

As already mentioned, the division into a plurality of sectors 61, 62, 63 and in these differently arranged planes 71, 72, 73, 74 is intended to achieve the most comprehensive possible irradiation of the surface of the handrail 17. Accordingly, it is also advantageous if said surface or the handrail 17 is always guided through the pass-through segment 57 at equal distances from the planes 71, 72, 73, 74.

Figure 8:
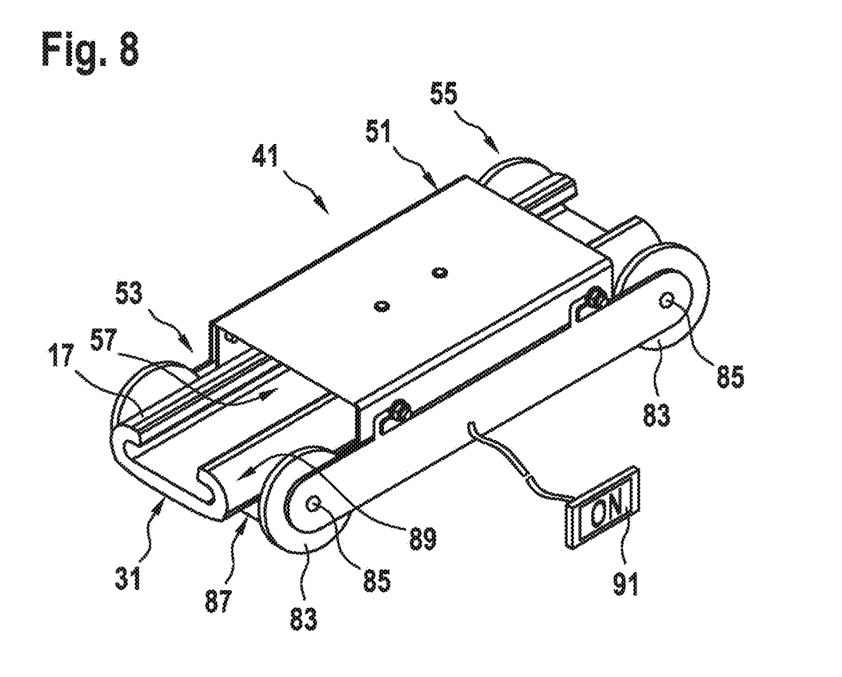
FIG. 8 shows a possible development of the handrail disinfecting device shown in FIGS. 1 to 7 with guide rollers on its entry side and exit side.

As shown in FIG. 8, at least one guide roller 83 can therefore be arranged on the entry side 53 and on the exit side 55 of the handrail disinfecting device 41. Said guide rollers 83 allow a handrail 17 of a passenger transport installation 1 to be guided through the housing 51 in the pass-through segment 57 in a defined position.

As shown in FIG. 8, handrails 17 for passenger transport installations 1 usually have a C-shaped cross section, with the most touched and therefore most contaminated region being its broad rear surface 31. Said broad rear surface is preferably supported by the guide roller 83 and is irradiated as directly as possible by the light-emitting diodes 43 arranged on the first plane 71 by directing the main light cone axes 47 of said diodes as orthogonally as possible relative to the rear surface 31. In order to achieve this, the axis of rotation 85 of the guide roller 83 is arranged in parallel with the first plane 71 and orthogonally to the pass-through segment 57.

Furthermore, a tread contour 87 of the guide roller 83 can correspond to an outer surface contour 89 of the handrail 17 to be guided. As a result, the handrail 17 is not only guided with more precise positioning through the housing 51, but the guide roller 83 having a correspondingly adapted tread contour 87 also serves as radiation protection because hardly any electromagnetic radiation can escape from the housing 51 through the narrow gap between the handrail 17 and the tread contour 87.

Because the germicidal electromagnetic radiation emitted by the light-emitting diodes 43 is in the ultraviolet light range, correct operation of the handrail disinfecting device 41 can hardly be visually recognized, and certainly not when said handrail disinfecting device is installed in the balustrade base 13, hidden from the users. In order to display the operating status of the handrail disinfecting device 41, a suitable display device 91 can therefore be provided, which can then be arranged, for example, in the access regions 3 (see FIG. 1) such that they are clearly visible to the users.

As shown in FIG. 1, the step belt 9 and the handrails 17 are driven by a drive unit 7. The drive unit 7 includes a drive motor 21 that is controlled by a drive controller 19 of the passenger transport installation 1. Because of the speed signal that is generated by the drive controller 19 and sent to a converter (not shown) in order to correspondingly control the drive motor 21, the current speed of the handrail 17 is available in the drive controller 19 at any time. The drive controller 19 can now also be configured to operate the handrail disinfecting device 41. Specifically, the light-emitting diodes 43 of the individual sectors 61, 62, 63 can be controlled according to the speed signal from the drive controller 19 in order to minimize the energy consumption of the light-emitting diodes 43 and the damaging effect of the germicidal electromagnetic radiation on the material of the handrail 17 while always maintaining an optimal disinfecting effect.

Although FIGS. 1 to 8 show different aspects of the present disclosure on the basis of a passenger transport installation 1 which is designed as an escalator and is intended to connect floors E1, E2 that are vertically spaced apart from one another, it is obvious that the handrail disinfecting device 41 and the corresponding method steps described can also be used for obliquely arranged moving walkways or horizontally arranged moving walkways. In addition, further sectors 61, 62, 63 having at least one plane 71, 72, 73 can be arranged upstream of the first sector 61 and/or downstream of the third sector 63. Of course, a plurality of handrail disinfecting devices 41 can also be arranged one behind the other in the balustrade base 13 for each handrail 17.

Finally, it should be noted that terms such as "comprising," "having," etc., do not preclude other elements or steps and terms such as "a" or "an" do not preclude a plurality. Furthermore, it should be noted that features or steps that have been described with reference to one of the above embodiments may also be used in combination with other features or steps of other embodiments described above. Reference signs in the disclosure or claims should not be considered to be limiting.

The invention claimed is:

1. A handrail disinfecting device, comprising:
at least one housing; and
a plurality of light-emitting diodes having a main light cone axis, which light-emitting diodes can emit germicidal electromagnetic radiation in the region of their light cone,
wherein the housing has an entry side and an exit side opposite the entry side for a continuous handrail of a passenger transport installation,
wherein a pass-through segment for the handrail, which segment is divided into at least two sectors, is present in the housing between the entry side and the exit side;
wherein the sectors are arranged one behind the other in the longitudinal extension of the pass-through segment;
wherein at least one light-emitting diode is arranged in the first sector, the main light cone axis of which diode is oriented substantially orthogonally to a first plane; and
wherein at least two light-emitting diodes are arranged in the second sector, wherein the main light cone axis of at least one light-emitting diode is oriented substantially orthogonally to a second plane and the main light cone axis of at least one light-emitting diode is oriented substantially orthogonally to a third plane, and
wherein the second plane and the third plane are arranged in parallel with the longitudinal extension of the pass-through segment and so as to be mutually inclined at an angle of 100° to 160°,
and wherein the handrail disinfecting device has at least one guide roller, by means of which guide roller a handrail of a passenger transport installation can be guided through the housing in the pass-through segment in a defined position in relation to the light-emitting diodes.

2. The handrail disinfecting device according to claim 1, wherein at least one guide roller is arranged on the entry side and/or on the exit side.

3. The handrail disinfecting device according to claim 1, wherein at least one guide roller is arranged inside the housing.

4. The handrail disinfecting device according to claim 1, wherein the inclination of the second plane relative to the first plane is the same as the inclination of the third plane relative to the first plane.

5. The handrail disinfecting device according to claim 1, wherein a third sector is defined in the pass-through segment, in which sector at least one light-emitting diode is arranged, the main light cone axis of which is oriented orthogonally to a fourth plane, wherein the second sector is arranged between the first and the third sector, and the fourth plane is arranged in parallel with the first plane.

6. The handrail disinfecting device according to any of claim 1, wherein at least three light-emitting diodes are arranged in each plane, and wherein their main light cone axes are oriented in parallel with one another in each plane.

7. The handrail disinfecting device according to claim 6, wherein five light-emitting diodes are arranged in the first plane, three light-emitting diodes each are arranged in the second and the third plane and four light-emitting diodes are arranged in the fourth plane, if present.

8. The handrail disinfecting device according to claim 1, wherein the housing is comprises a U-shaped main housing part and a cover spanning the open side of the main housing part.

9. The handrail disinfecting device according to claim 1, wherein said handrail disinfecting device comprises a carrier, which is arranged in the housing below the pass-through segment with respect to the intended installation position of the handrail disinfecting device, on which carrier all planes present are formed, and wherein the light-emitting diodes are fastened to said planes.

10. The handrail disinfecting device according to claim 1, wherein at least one reflector which is directed toward the pass-through segment and is intended for reflecting the radiation is arranged in the housing.

11. The handrail disinfecting device according to claim 1, wherein an axis of rotation of the guide roller is arranged in parallel with the first plane and orthogonally to the pass-through segment.

12. The handrail disinfecting device according to claim 1, wherein a tread contour of the guide roller corresponds to an outer surface contour of the handrail to be guided.

13. The handrail disinfecting device according to any of claim 1, wherein the angle of the mutually inclined second and third plane is matched to the spectral composition of the germicidal electromagnetic radiation of the light-emitting diodes and the material surface of the handrail.

14. A passenger transport installation configured as an escalator or a moving walkway, comprising at least one balustrade that comprises at least one circulating handrail, wherein the passenger transport installation has at least one handrail disinfecting device according to claim 1 for each circulating handrail.

15. The passenger transport installation according to claim 14, wherein the balustrade comprises a balustrade base in which a returning run of the handrail is guided so as to be concealed from the users of the passenger transport installation, and wherein the handrail disinfecting device is installed in the balustrade base of the balustrade.

\* \* \* \* \*

UNITED STATES PATENT AND TRADEMARK OFFICE
CERTIFICATE OF CORRECTION

PATENT NO. : 11,970,366 B2
APPLICATION NO. : 17/802801
DATED : April 30, 2024
INVENTOR(S) : Georg Wagenleitner Page 1 of 1

It is certified that error appears in the above-identified patent and that said Letters Patent is hereby corrected as shown below:

In the Claims

In Column 10, Claim 6, Line 52, after "according to" delete "any of".

In Column 11, Claim 13, Line 16, after "according to" delete "any of".

Signed and Sealed this
Thirty-first Day of December, 2024

Derrick Brent
*Acting Director of the United States Patent and Trademark Office*